United States Patent [19]

Ito et al.

[11] 4,276,308
[45] Jun. 30, 1981

[54] METHOD FOR CONTROLLING WOOD-DAMAGING INSECTS

[75] Inventors: Takaaki Ito, Kobe; Tokio Watanabe, Hirakata, both of Japan

[73] Assignee: Sumitomo Chemical Company, Limited, Osaka, Japan

[21] Appl. No.: 104,995

[22] Filed: Dec. 18, 1979

[30] Foreign Application Priority Data

Dec. 25, 1978 [JP] Japan ................... 53-163615

[51] Int. Cl.$^3$ ............................................ A01N 37/34
[52] U.S. Cl. ................................. 424/304; 106/18.32; 106/18.35
[58] Field of Search .................... 424/304; 106/18.32, 106/18.35

[56] References Cited

U.S. PATENT DOCUMENTS

| 3,835,176 | 9/1974 | Matsuo et al. | 424/304 |
| 4,058,622 | 11/1977 | Fujimoto et al. | 424/304 |

OTHER PUBLICATIONS

Botyu-Kagaku, vol. 41, 138–142 (1976).
Pestic. Sci., 8, 284–290 (1977).

*Primary Examiner*—Lorenzo B. Hayes

*Attorney, Agent, or Firm*—Sughrue, Rothwell, Mion, Zinn and Macpeak

[57] ABSTRACT

A method for controlling insects harmful to wood comprising contacting the insect with a composition comprising a carboxylate of the formula:

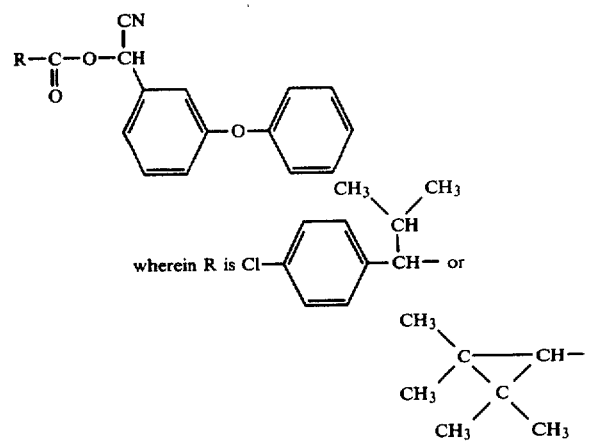

as an active ingredient.

4 Claims, No Drawings

METHOD FOR CONTROLLING WOOD-DAMAGING INSECTS

BACKGROUND OF THE INVENTION

1. Field of the Invention

The present invention relates to excellent wood preservative compositions comprising a carboxylate of the formula (I):

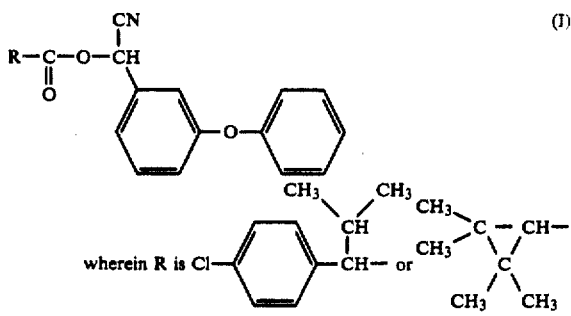

as an active ingredient.

2. Description of the Prior Art

Wood, used as a building material for houses, construction, necessities, furniture, common industrial materials and the like, is damaged by various insects or microorganisms. Particularly, wood is damaged by termites and lauan and Japanese oak are damaged by powder-post beetles. Hitherto, dieldrin and BHC have been used to prevent this damage, but these compounds have a strong toxicity and present a danger of environmental pollution and for this reason their use has been gradually limited.

For the reasons described above, extensive studies have been directed to wood preservative compositions which can be used safely and with high effectiveness. As a result, it has been found that compositions containing a carboxylate of the foregoing formula (I) have excellent properties in the preservation of wood.

The carboxylate of the formula (I) according to the present invention not only has an excellent insecticidal activity but also an excellent ability to maintain its activity, as is apparent from the examples described hereinafter, as compared with chlordane, a typical insecticidal compound most commonly used to control insects harmful to wood. Also, it has the advantage of low toxicity. Consequently, the esters are excellent as wood preservatives.

DETAILED DESCRIPTION OF THE INVENTION

By mixing the carboxylate (I) of the present invention and a fungicide compositions which are very advantageous as wood preservatives and in addition combine a fungicidal effect can be produced. Representative fungicides include chloronaphthalene, pentachlorophenyl laurate, pentachlorophenol, p-nitrophenol, cloro-o-phenylphenol, o-phenylphenol, creosote, aluminum salt of N-nitroso-N-cyclohexylhydroxylamine, tribromophenol, tributyltin oxide, tributyltin phthalate, triphenyltin oxide, diiodomethyl p-tolyl sulfon, zinc naphthenate, copper naphthenate, copper 8-oxyquinoline and dinitrocresol.

The wood preservative compositions of the present invention are easily produced by conventional methods for producing common wood preservatives (e.g., wood exterminators, preventives, soil treatment agents, antiseptic and insectproof produced by mixing a carboxylate (I) of the present invention with a wood fungicide if necessary, dissolving the mixture in a solvent (e.g., kerosene, dodecylbenzene, xylene, deodorized kerosene, etc.), adding an emulsifier or dispersing agent (e.g., a nonionic or anionic surface active agent), adsorbing agent (e.g., white carbon, diatomaceous earth, etc.), binder (e.g., paraffins, Polybutene HV-300, etc.) or wetting agent (e.g., a nonionic surface active agent, etc.) to the resulting solution which may previously be adsorbed into a suitable solid carrier (e.g., diluents such as clay, talc, vegetable powders, mineral powders, etc.) and formulating preparations such as oil sprays, emulsifiable concentrates, wettable powders, dusts, granules tablets and aerosols. Further, the insecticidal activity can be strengthened and stabilized by adding a synergist and a stabilizer.

Multi-purpose compositions can be produced by mixing other substances having a biological activity with the carboxylate (I) of the present invention.

Conventional techniques commonly applied to the conventional chlordane-containing wood preservatives may be used in the application of the wood preservative composition of the present invention. For example, the wood may be dipped in the composition of the present invention or sprayed or coated therewith so that the amount of the composition attached, coated or absorbed in the wood is about 100 to 250 g (as a 0.1 to 1% oil spray) per $m^2$ of the wood, followed by air-drying or heat-drying. When contact between wood and soil is unavoidable such as in the case of wood piles or wood buried in soil, an aqueous dilute solution containing the present composition in an amount of from 0.1 to 1.0% may be mixed with or injected into soil around the wood in a rate of 1 to 10 liters per $m^2$ of the soil surface. On the other hand, when insects attack or approach wood, the present composition may be mixed with a paint and then coated.

The concentration of the carboxylate (I) of the present invention as the active ingredient in the wood preservative composition is usually from 0.1 to 80% by weight, although higher or lower concentration may be employed.

Specific examples of the carboxylate (I) of the present invention include the compounds described below. The present invention will be illustrated with reference to the following preparation examples and examples. But the present invention is of course not limited to these examples.

Compound (1) α-Cyano-3-phenoxybenzyl 2-(4-chlorophenyl)-isovalerate

Compound (2) α-Cyano-3-phenoxybenzyl 2-(S)-(4-chlorophenyl)-isovalerate

Compound (3) (S)-α-Cyano-3-phenoxybenzyl 2-(S)-(4-chlorophenyl)isovalerate

Compound (4) α-Cyano-3-phenoxybenzyl 2,2,3,3-tetramethylcyclopropane-1-carboxylate Compounds (1) to (3) have the following formula:

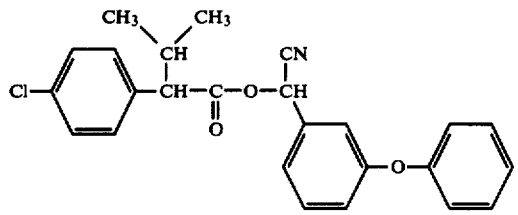

and Compound (4) has the following formula:

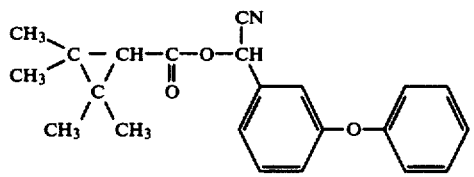

Preparations in accordance with the present invention are illustrated below. All parts in the following preparation examples and examples are by weight.

PREPARATION EXAMPLE 1: OIL SPRAY 0.5 part of each of Compounds (1), (2), (3) and (4) and 25 parts of ethylene dibromide (penetrating agent) were dissolved in kerosene and diluted to 100 parts with kerosene to obtain oil sprays of each compound.

PREPARATION EXAMPLE 2: OIL SPRAY 0.5 part of Compound (1) and 5 parts of 4,6-dinitrocresol (wood fungicide) were dissolved in kerosene and diluted to 100 parts with kerosene to obtain an oil spray.

PREPARATION EXAMPLE 3: OIL SPRAY 0.5 part of Compound (1) and 1 part of pentachlorophenyl laurate (wood fungicide) were dissolved in kerosene and diluted to 100 parts with kerosene to obtain an oil spray.

PREPARATION EXAMPLE 4: OIL SPRAY 0.5 part of Compound (1) or (4) and 1 part of the aluminum salt of N-nitroso-N-cyclohexylhydroxylamine (wood fungicide) were dissolved in dodecylbenzene and diluted to 100 parts with dodecylbenzene to obtain an oil spray.

PREPARATION EXAMPLE 5: OIL SPRAY 0.5 part of Compound (4), 0.5 part of copper 8-oxyquinoline (wood fungicide) and 1.5 parts of nickel octylate were dissolved in xylene and diluted to 100 parts with xylene to obtain an oil spray.

PREPARATION EXAMPLE 6: OIL SPRAY 0.5 part of Compound (1) and 1 part of diiodomethyl p-tolyl sulfon (wood fungicide) were dissolved in xylene and diluted to 100 parts with xylene to obtain an oil spray.

PREPARATION EXAMPLE 7: OIL SPRAY 0.5 part of Compound (4) and 0.5 part of chloronaphthalene (wood fungicide) were dissolved in xylene and diluted to 100 parts with xylene to obtain an oil spray.

PREPARATION EXAMPLE 8: OIL SPRAY 0.5 part of Compound (1), 2 parts of tribromophenol (wood fungicide) and 2 parts of cyclohexanone were dissolved in xylene and diluted to 100 parts with xylene to obtain an oil spray.

PREPARATION EXAMPLE 9: EMULSIFIABLE CONCENTRATE 10 parts of each of Compounds (1), (2), (3) and (4), 20 parts of Sorpol SM 100P (emulsifier, a registered trademark of Toho Chemical Co., Ltd.) and 70 parts of xylene were mixed to obtain emulsifiable concentrates of each compound.

PREPARATION EXAMPLE 10: EMULSIFIABLE CONCENTRATE 60 parts of each of Compounds (1), (2), (3) and (4), 10 parts of Sorpol SM 100P (emulsifier, a registered trademark of Toho Chemical Co., Ltd.) and 30 parts of xylene were mixed to obtain emulsifiable concentrates of each compound.

PREPARATION EXAMPLE 11: EMULSIFIABLE CONCENTRATE 5 parts of Compound (1), 5 parts of tributyltin oxide (wood fungicide), 10 parts of Sorpol 3005X (a registered trademark of Toho Chemical Co., Ltd.) and 80 parts of xylene were mixed to obtain an emulsifiable concentrate.

PREPARATION EXAMPLE 12: AEROSOL 0.5 part of Compound (1), 2 parts of chlordane and 0.5 part of a perfume were dissolved in 40 parts of deodorized kerosene and filled in an aerosol container. After attaching a valve portion to the container, 57 parts of propellant (liquefied petroleum gas) was charged therein under pressure to obtain an aerosol.

PREPARATION EXAMPLE 13: AEROSOL 0.5 part of Compound (1) or (4), 5 parts of methylchloroform (co-solvent) and 0.5 part of a perfume were dissolved in 36 parts of deodorized kerosene and filled in an aerosol container. After attaching a valve portion to the container, 58 parts of propellant (liquefied petroleum gas) was charged therein under pressure to obtain aerosols.

PREPARATION EXAMPLE 14: WETTABLE POWDER 10 parts of Compound (1) and 2 parts of Sorpol 2495G (emulsifier, a registered trademark of Toho Chemical Co., Ltd.) were mixed, and then 10 parts of white carbon and 78 parts of 30-mesh diatomaceous earth were added thereto. The mixture was well mixed with stirring to obtain a wettable powder.

PREPARATION EXAMPLE 15: DUST 2 parts of Compound (1) was dissolved in acetone and added to a mixture of 0.3 part of isopropyl acid-phosphate (PAP: produced by Nippon Chemical Industrial Co., Ltd.), 1 part of white carbon and 96.7 parts of clay. After stirring, acetone was removed by evaporation to obtain a dust.

PREPARATION EXAMPLE 16: GRANULE 93 parts of 50- to 150-mesh pumice is added to a mixture of 5 parts of Compound (1) and 2 parts of Polybutene HV-300 (sticking agent, a registered trademark of Nisseki Jushi Kagaku Co.). The resulting mixture was mixed with stirring and dried to obtain a granule.

EXAMPLE 1

Insecticidal Activity

The oil sprays and emulsifiable concentrates were each uniformly applied to a filter paper 9 cm in diameter (No. 5A, produced by Toyo Roshi Co.) at a rate of 50 g/m$^2$, the oil spray being applied as it was and the emulsifiable concentrate as an aqueous dilute solution. After standing for 2 hours, the workers of Japanese termite (*Leucotermes speratus* Kolbe) were liberated and covered with a Petri dish, and the mortalities after 3 hours and 24 hours were observed. As a standard, permethrin and chlordane prepared according to Preparation Examples (9) and (1), respectively, were used.

TABLE 1

| Run No. | Test Compound | Preparation | Preparation Example No. | Effective Concentration of Test Compound (%) | Mortality After 3 Hours (%) | Mortality After 24 Hours (%) |
|---|---|---|---|---|---|---|
| 1 | Compound (1) | Oil spray | 1 | 0.5 | 34 | 100 |
| 2 | Compound (2) | Oil spray | 1 | 0.5 | 60 | 100 |
| 3 | Compound (3) | Oil spray | 1 | 0.5 | 80 | 100 |
| 4 | Compound (4) | Oil spray | 1 | 0.5 | 73 | 100 |
| 5 | Compound (1) | Oil spray | 2 | 0.5 | 23 | 100 |
| 6 | Compound (1) | Oil spray | 3 | 0.5 | 79 | 100 |
| 7 | Compound (1) | Oil spray | 4 | 0.5 | 39 | 100 |
| 8 | Compound (4) | Oil spray | 5 | 0.5 | 83 | 100 |
| 9 | Compound (1) | Emulsifiable concentrate | 9 | 0.05 | 0 | 63 |
|   |   |   |   | 0.1 | 0 | 100 |
| 10 | Compound (4) | Emulsifiable concentrate | 9 | 0.05 | 3 | 98 |
|   |   |   |   | 0.1 | 24 | 100 |
| 11 | Permethrin | Emulsifiable concentrate | 9 | 0.05 | 0 | 26 |
|   |   |   |   | 0.1 | 0 | 89 |
| 12 | Chlordane (2%) | Oil spray | 1 | 2.0 | 7 | 100 |
| 13 | Untreated | — | — | — | 0 | 0 |

These results show that each composition of the present invention has an excellent insecticidal activity.

EXAMPLE 2

Insecticidal Activity

The emulsifiable concentrates of Compounds (1), (2), (3) and (4) obtained in Preparation Example 9 were diluted with water and uniformly applied to the surface (10×10 cm) of a lauan plate at a rate of 100 ml/m$^2$ by means of a pipette. After air-drying for 2 days, powderpost beetle larvae (*Lyctus brunneus* Stephens) were brought into contact with the treated surface, and the mortality was observed with the lapse of time.

The emulsifiable concentrates of chlordane and permethrin prepared according to Preparation Example 9 were used as a standard.

TABLE 2

| Test Compound | Concentration of Test Compound (%) | Mortality After 1 Day (%) | Mortality After 2 Days (%) | Mortality After 4 Days (%) |
|---|---|---|---|---|
| Compound (1) | 0.006 | 0 | 0 | 0 |
|   | 0.025 | 12 | 12 | 17 |
|   | 0.1 | 34 | 43 | 43 |
|   | 0.4 | 50 | 68 | 77 |
| Compound (2) | 0.006 | 0 | 7 | 13 |
|   | 0.025 | 27 | 53 | 57 |
|   | 0.1 | 37 | 87 | 87 |
|   | 0.4 | 87 | 97 | 100 |
| Compound (3) | 0.006 | 27 | 27 | 33 |
|   | 0.025 | 43 | 53 | 60 |
|   | 0.1 | 69 | 86 | 98 |
|   | 0.4 | 97 | 100 | 100 |
| Compound (4) | 0.006 | 0 | 7 | 20 |
|   | 0.025 | 69 | 86 | 97 |
|   | 0.1 | 80 | 97 | 100 |
|   | 0.4 | 100 | 100 | 100 |
| Permethrin | 0.006 | 0 | 0 | 7 |
|   | 0.025 | 0 | 27 | 30 |
|   | 0.1 | 37 | 70 | 70 |
|   | 0.4 | 43 | 86 | 97 |
| Chlordane | 0.6125 | 0 | 0 | 3 |
|   | 2.5 | 0 | 10 | 27 |
|   | 10 | 0 | 25 | 77 |
| Untreated | — | 0 | 0 | 10 |

It is apparent from the table that Compounds (1) to (4) have a strong insecticidal activity against powderpost beetle larvae.

EXAMPLE 3

Preventive Efficacy

Hemlock spruce shavings of 2×2×0.1 mm were dipped for 30 seconds in each of the oil sprays and emulsifiable concentrates, the oil spray being used as it was and the emulsifiable concentrate as an aqueous dilute solution. After air-drying for a week, they were placed with 50 workers of Japanese termite (*Leucotermes speratus* Kolbe), in a wide-mouth glass bottle containing sandy loam, and covered with a lid. After 2 weeks, the degree of damage of hemlock spruce was evaluated according to the following equation. As a standard the emulsifiable concentrates of chlordane and permethrin prepared according to Preparation Example 9 were used.

$$\text{Degree of damage} = \frac{\text{Weight Before} - \text{Weight After}}{\text{Weight Before}} \times 100$$

TABLE 3

| Run No. | Test Compound | Preparation | Preparation Example No. | Effective Concentration of Test Compound (%) | Degree of Damage |
|---|---|---|---|---|---|
| 1 | Compound (1) | Oil spray | 1 | 0.5 | 0 |
| 2 | Compound (2) | Oil spray | 1 | 0.5 | 0 |
| 3 | Compound (3) | Oil spray | 1 | 0.5 | 0 |
| 4 | Compound (4) | Oil spray | 1 | 0.5 | 0 |
| 5 | Compound (4) | Oil spray | 5 | 0.5 | 0 |
| 6 | Compound (1) | Oil spray | 6 | 0.5 | 0 |
| 7 | Compound (1) | Emulsifiable concentrate | 9 | 0.016 | 0 |
| 8 | Compound (1) | Emulsifiable concentrate | 9 | 0.008 | 13 |
| 9 | Compound (4) | Emulsifiable concentrate | 9 | 0.016 | 0 |
| 10 | Compound (4) | Emulsifiable concentrate | 9 | 0.008 | 5 |
| 11 | Permethrin | Emulsifiable concentrate | 9 | 0.016 | 5 |
| 12 | Permethrin | Emulsifiable concentrate | 9 | 0.008 | 19 |
| 13 | Chlordane | Emulsifiable concentrate | 9 | 0.016 | 7 |
| 14 | Chlordane | Emulsifiable concentrate | 9 | 0.008 | 36 |
| 15 | Untreated | | — | — | 78 |

These results show that Compounds (1) to (4) have an excellent preventive efficacy as compared with chlordane and permethrin.

EXAMPLE 4

Preventive Efficacy

Lauan sapwood (starch content 2% or more) was cut into a block, $2 \times 2 \times 2$ cm, which was then coated with a paint at the section. The emulsifiable concentrates of Compounds (1) and (4) obtained in Preparation Example 9 were diluted with water to a predetermined concentration and the sapwood block was dipped in the aqueous solution for 30 seconds. After air-drying for 3 days, two pairs of powder-post beetle adults (*Lyctus brunneus* Stephens) were released. After 3 months, the sapwood was examined for the presence of damage in its inner part. As a control, the emulsifiable concentrates of chlordane and permethrin prepared according to Preparation Example 9 were used.

TABLE 4

| Test Compound | Concentration of Test Compound (%) | Number of Damaged Blocks/3 Blocks |
|---|---|---|
| Compound (1) | 0.1 | 0 |
| | 0.02 | 0 |
| | 0.004 | 0 |
| | 0.0008 | 2 |
| Compound (4) | 0.1 | 0 |
| | 0.02 | 0 |
| | 0.004 | 0 |
| | 0.0008 | 3 |
| Permethrin | 0.1 | 0 |
| | 0.02 | 0 |
| | 0.004 | 1 |
| | 0.0008 | 2 |
| Chlordane | 0.1 | 0 |
| | 0.02 | 1 |
| | 0.004 | 3 |
| | 0.0008 | 3 |
| Untreated | | 3 |

The table shows that Compounds (1) and (4) have an excellent effect against powder-post beetles as compared with chlordane and permethrin.

EXAMPLE 5

Residual Efficacy

The aerosol prepared according to Preparation Example 13 was sprayed for 3 seconds, 30 cm apart, on the surface ($30 \times 10$ cm) of lauan plate. After a predetermined period of time, 20 workers of Japanese termite (*Leucotermes speratus* Kolbe) were brought into contact with the treated surface, and the mortality after 24 hours was obtained.

The contact treatment was carried out under 100% of relative humidity. As a standard, an aerosol prepared as described in Preparation Example 12 but using no Compound (1), was used.

TABLE 5

| | Mortality | | | |
|---|---|---|---|---|
| Test Compound | 0 Day (%) | 30 Days (%) | 60 Days (%) | 90 Days (%) |
| Aerosol Preparation Example 12 | 100 | 100 | 100 | 100 |
| Aerosol Preparation Example 13 (Compound (1)) | 100 | 100 | 100 | 100 |
| Aerosol Preparation Example 12 Containing no Compound (1) | 100 | 100 | 60 | 3.3 |
| Untreated | 3.3 | 0 | 0 | 6.6 |

It is clearly recognized from the table that Compound (1) has a very long residual efficacy.

EXAMPLE 6

Wood Fungicidal Efficacy

This test was carried out according to JIS (A) 9302 "Method for Testing Effectiveness of Wood Fungicides against Decay of Wood". The oil spray obtained in Preparation Example 3 was injected under reduced pressure into a test piece ($2 \times 2 \times 1$ cm) of Japan cedar sapwood (amount absorbed 200%). Thereafter, ten cycles of a weathering test (with 1 hour's dipping in water and 60° C. for 23 hours' drying as one cycle) were applied to the test piece which was then inoculated with test fungi, *Tyromices palustris* and *Coriolus versicolor* Murr. After 90 days' culture, weight reduction by the test fungus was measured to obtain the wood fungicidal efficacy of the test compound. The weight reduction was obtained according to the following equation:

wood fungicidal effective value =

$$\frac{\left[\begin{array}{c}\text{Mean weight}\\\text{reduction of}\\\text{untreated}\\\text{test piece (\%)}\end{array}\right] - \left[\begin{array}{c}\text{Mean weight}\\\text{reduction of}\\\text{treated test}\\\text{piece (\%)}\end{array}\right] - \left[\begin{array}{c}\text{Mean weight}\\\text{reduction of}\\\text{treated test}\\\text{piece of}\\\text{correction (\%)}\end{array}\right]}{\text{Mean weight reduction of untreated test piece (\%)}} \times 100$$

TABLE 6

| Test Compound | Test Fungi | Number of Weathering Test | Amount Absorbed (%) | Weight Reduction (%) | Wood Fungicidal Effective Value | Area* |
|---|---|---|---|---|---|---|
| Oil spray Preparation Example 3 | Tyromices palustris | 0 | 203 | 0 | 99 | |
| | | 10 | 207 | 0 | 97 | A |
| | Coriolus versicolor | 0 | 209 | 0 | 95 | |
| | | 10 | 205 | 0 | 93 | |
| No treatment | Tyromices palustris | 0 | — | 47 | — | |
| | | 10 | — | 48 | — | |
| | Coriolus versicolor | 0 | — | 24 | — | |
| | | 10 | — | 27 | — | |

*The efficiency area of the wood fungicidal efficacy by JIS (A) 9302 "Method for Testing Effectiveness of Wood Preservatives against Decay of Wood".

The table shows that the oil spray obtained in Preparation Example 3 has an excellent wood preservative property.

EXAMPLE 7

Preventive Efficacy

The oil spray of Compound (1) or (4) prepared according to Preparation Example 4 was diluted with dodecylbenzene to a predetermined concentration and painted on a surface of pine wood, 30×5×5 cm, at a rate of 300 ml/m². The treated sticks were buried about 30 cm below the surface of the ground around a nest of formosan subterranean termite (*Coptotermes formosanus* Shiraki). After 1 year, the degree of damage of the sticks was scored according to the damage-index (0: no damage and 8: disappearance of stick) as a standard, permethrin prepared as described in Preparation Example 4 was used. Experiments were repeated 5 times.

Damage Index

0: No trace of termite approach to wood stick
1: Trace of termite approach to wood stick without damage
2: Slight damage only on surface of wood stick
3: Slight damage at inner part of wood stick
4: Moderate damage on surface of wood stick
5: Moderate damage at inner part of wood stick
6: Heavy damage but still able to observe original form of wood stick
7: Serious damage and original form of wood stick destroyed
8: No appearance of wood stick

| Test Location | Compound | Concentration (%) | Run No. and Damage | | | | |
|---|---|---|---|---|---|---|---|
| | | | 1 | 2 | 3 | 4 | 5 |
| A | (1) | 0.1 | 0 | 0 | 0 | 0 | 0 |
| | | 0.2 | 0 | 0 | 0 | 0 | 0 |
| | | 0.4 | 0 | 0 | 0 | 0 | 0 |
| | Untreated | — | 5 | 5 | 5 | 8 | 5 |
| B | (4) | 0.1 | 0 | 0 | 0 | 0 | 0 |
| | | 0.2 | 0 | 0 | 0 | 0 | 0 |
| | | 0.4 | 0 | 0 | 0 | 0 | 0 |
| | Untreated | — | 7 | 7 | 6 | 6 | 7 |
| C | Permethrin | 0.1 | 2 | 2 | 1 | 2 | 4 |
| | | 0.2 | 0 | 0 | 0 | 0 | 0 |
| | | 0.4 | 0 | 0 | 0 | 0 | 0 |
| | Untreated | — | 7 | 8 | 5 | 5 | 6 |

It is obvious from these results that Compounds (1) and (4) show higher preventive efficacy against formosan subterranean termite in comparison to permethrin.

While the invention has been described in detail and with reference to specific embodiments thereof, it will be apparent to one skilled in the art that various changes and modifications can be made therein without departing from the spirit and scope thereof.

What is claimed is:

1. A method for controlling insects harmful to wood including termites and powder-post beetles which comprises contacting the insects with a compound represented by the formula:

$$R-\underset{\underset{O}{\|}}{C}-O-\underset{\underset{}{}}{CH}(CN)(\text{3-phenoxyphenyl})$$

wherein R is $$Cl-\underset{}{\phantom{X}}\text{-phenyl-}\underset{CH_3}{\underset{|}{CH}}-\underset{CH_3}{\underset{|}{CH}}- \text{ or}$$

$$\underset{CH_3}{\underset{|}{\underset{CH_3}{\overset{|}{C}}}}-\text{cyclopropyl-}CH_3, CH_3$$

2. The method according to claim 1, wherein the compound is α-cyano-3-phenoxybenzyl 2-(S) (4-chlorophenyl)isovalerate.

3. The method according to claim 1, wherein the compound is (S)-α-cyano-3-phenoxybenzyl 2-(S) (4-chlorophenyl)isovalerate.

4. A method for controlling insects harmful to wood according to claim 1, wherein the insects are lyctus powder-post beetle (*Lyctus brunneus* Stephens), Japanese termite (*Leucotermes speratus* Kolbe) and formosan subterranean termite (*Coptotermes formosanus* Shiraki).

* * * * *